United States Patent [19]

Ark et al.

[11] 4,172,852

[45] Oct. 30, 1979

[54] PROCESS FOR PREPARING A MIXTURE OF AROMATIC SULFONES AND AROMATIC SULFONYL CHLORIDES

[75] Inventors: Wong F. Ark, Bridgewater; James H. Kawakami, Piscataway; Ulrich A. Steiner, North Plainfield, all of N.J.

[73] Assignee: Union Carbide Corporation, New York, N.Y.

[21] Appl. No.: 824,705

[22] Filed: Aug. 15, 1977

[51] Int. Cl.$^2$ .................. C07C 147/06; C07C 143/70
[52] U.S. Cl. ......................... 260/607 AR; 260/543 R
[58] Field of Search ..................... 260/543 R, 607 AR

[56] References Cited

U.S. PATENT DOCUMENTS 3,701,806  10/1972  Keough et al. .................. 260/543 R

OTHER PUBLICATIONS

Kittila, "Dimethylformamide Chemical Uses," DuPont & Co., Chapter 16, pp. 76–77.
Bosshard et al., Helvetica Chimica Acta XLII, 1653, (1959).

*Primary Examiner*—Gerald A. Schwartz

*Attorney, Agent, or Firm*—Franklyn Schoenberg

[57] ABSTRACT

A process is provided for producing a mixture of aromatic sulfonyl chlorides and aromatic sulfones substantially free of the corresponding aromatic sulfonic acids and their anhydrides, which comprises the steps of (a) reacting a monosubstituted benzene such as monochlorobenzene with sulfur trioxide in the presence of at least about 15 mole percent to about 50 mole percent of thionyl chloride, based on the sulfur trioxide, at a temperature from about the freezing point of the reactants to about 40° C.; (b) adding to the reaction mixture of step (a) at least about 60 mole percent thionyl chloride, based on the sulfur trioxide, and preferably a small catalytic amount of dimethylformamide, wherein the total thionyl chloride in the reaction mixture is at least about 110 mole percent, based on the sulfur trioxide, while maintaining the reaction mixture at a temperature between about 25° C. and 70° C.; and then (c) continuing the reaction up to a temperature of about 160° C. The mixture produced can be used without further purification to form diaryl sulfones in high yield, for example, by reacting with monochlorobenzene in the presence of ferric chloride.

5 Claims, No Drawings

PROCESS FOR PREPARING A MIXTURE OF AROMATIC SULFONES AND AROMATIC SULFONYL CHLORIDES

The present invention relates to an improved process for the preparation of mixtures of aromatic sulfones and sulfonyl chlorides, and more particularly to an improved process for preparing mixtures of aromatic sulfones and sulfonyl chlorides, essentially free of the corresponding aromatic sulfonic acid or its respective anhydride, which are especially suitable for the preparation of 4,4'-dichlorodiphenyl sulfone.

Diaryl sulfones are important and useful organic compounds. For example, 4,4'-dichlorodiphenyl sulfone is a monomer in the preparation of polysulfone resins such as the polyarylene polyethers disclosed in Belgian Pat. No. 650,476.

A commercially important method for the production of 4,4'-dichlorodiphenyl sulfone is described in U.S. Pat. No. 3,701,806 to Keogh et al. wherein a mixture of sulfonyl chlorides and aromatic sulfones is prepared from which 4,4'-dichlorodiphenyl sulfone can be readily isolated, or more importantly, can be further reacted with chlorobenzene in the presence of ferric chloride according to the process disclosed in U.S. Pat. No. 2,224,964 to produce 4,4'-dichlorodiphenyl sulfone in high overall yields. In the process described in the Keogh et al. patent a monosubstituted benzene having the formula

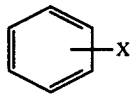

wherein X is H, fluoro, bromo, or methyl substituents, is reacted with sulfur trioxide ($SO_3$) in the presence of at least a stoichiometric amount of thionyl chloride ($SOCl_2$). The mixture formed thereby requires no further purification for substantially complete conversion to diaryl sulfones with catalysts such as $FeCl_3$, $AlCl_3$, $SbCl_3$, $SnCl_4$; and the like.

While representing a significant improvement over many of the processes for producing 4,4'-dichlorodiphenyl sulfone heretofore available, and offering a commercial advantage in that it was not required to isolate the intermediate products, the overall chemical efficiency of the process disclosed in Keogh et al. for preparing 4,4'-dichlorodiphenyl sulfone was found in the laboratory to be only about 86 percent, based on $SO_3$, and about 82 percent, based on $SO_3$, during commercial operations, with undesirable residue by-products also being produced. While the chemical efficiency of the process is not impractically low and the undesirable by-products can be separated, it suggests an area wherein significant improvements would be desirable.

In accordance with the present invention, there is provided an improved process for producing a mixture of aromatic sulfonyl chlorides and aromatic sulfones substantially free of the corresponding aromatic sulfonic acids and their anhydrides, which comprises the steps of:

(a) reacting a mono substituted benzene having the formula

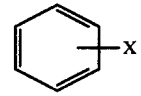

wherein X is hydrogen, fluoro, chloro, bromo or methyl with sulfur trioxide in the presence of at least about 15 mole percent to about 50 mole percent of thionyl chloride, and preferably between about 20 mole percent and 40 mole percent of thionyl chloride, based on the sulfur trioxide, at a temperature from about the freezing point of the reactants to about 40° C.;

(b) adding to the reaction mixture of step (a) at least about 60 mole percent thionyl chloride, based on the sulfur trioxide, and preferably a small catalytic amount of N,N-dimethylformamide, wherein the total thionyl chloride in the reaction mixture is at least about 110 mole percent, based on the sulfur trioxide, while maintaining the reaction mixture at a temperature between about 25° C. and 70° C.; and then (c) continuing the reaction up to a temperature at which excess thionyl chloride will be stripped from the reaction mixture, and preferably up to about 160° C.

It has been discovered that the process of the present invention will prepare an essentially pure mixture of aromatic sulfonyl chlorides and diaryl sulfones from which the diaryl sulfone can be readily separated or, more importantly, can be used without further purification to form the diaryl sulfones in high yields, as for example, by reacting with monochlorobenzene in the presence of ferric chloride according to the process disclosed in U.S. Pat. No. 2,224,964 to produce 4,4'-dichlorodiphenyl sulfone.

There is also provided in accordance with the present invention an improved process for preparing 4,4'-dichlorodiphenyl sulfone which comprises:

(a) reacting monochlorobenzene with sulfur trioxide in the presence of at least about 15 mole percent to about 50 mole percent of thionyl chloride, and preferably between about 20 mole percent and 40 mole percent, based on the sulfur trioxide, at a temperature from about the freezing point of the reactants to about 40° C.;

(b) adding to the reaction mixture of step (a) at least about 60 mole percent thionyl chloride based on the sulfur trioxide, and preferably a small catalytic amount of N,N-dimethylformamide, wherein the total thionyl chloride in the reaction mixture is at least about 110 mole percent, based on the sulfur trioxide, while maintaining the reaction mixture at a temperature between about 25° C. and 70° C.;

(c) continuing the reaction up to a temperature at which excess thionyl chloride will be stripped from the reaction mixture, and preferably up to about 160° C., and;

(d) reacting the products of step (c) with monochlorobenzene in the presence of ferric chloride catalyst to produce 4,4'-dichlorodiphenyl sulfone.

It has been discovered that when sulfur trioxide is reacted with mono substituted benzene in the presence of between about 15 mole percent and 50 mole percent of thionyl chloride based on the $SO_3$, which is substantially less than the stoichiometric amount of thionyl chloride based on the $SO_3$, the sulfonation reaction can be readily carried out. The subsequent addition of at least 60 mole percent of thionyl chloride based on $SO_3$, to the reaction mixture, which brings the thionyl chloride content of the reaction mixture to at least a stoichiometric excess of thionyl chloride based on the $SO_3$, yields a mixture of diaryl sulfone and aryl sulfonyl chloride that is substantially free of undesirable by-products, particularly when the reaction temperatures are relatively closely controlled or the reaction is carried out in the presence of a small catalytic amount of catalyst such as N,N-dimethylformamide. If, for example, it is then desired to completely convert the mixture to diaryl sulfones such as 4,4'-dichlorodiphenyl sulfone, reaction of the mixture with monochlorobenzene in the presence of a catalyst such as ferric chloride is quite facile and with high yields of the desired sulfone.

The overall chemical reactions that occur in the process are generally known. For instance, Wagner and Zook, in "Synthetic Organic Chemistry", John Wiley & Sons, Inc. (1953), on page 811, point out that sulfur trioxide reacts with aromatic hydrocarbons to produce the corresponding sulfonic acid with some sulfone as a by-product, and in Keogh et al. it is disclosed that reacting a mono-substituted benzene with sulfur trioxide in the presence of at least a stoichiometric excess of thionyl chloride produces a mixture of aromatic sulfonyl chloride and diaryl sulfone. The reaction of p-chlorobenzenesulfonic acid with thionyl chloride in the presence of at least molar amounts of dimethylformamide to produce p-chlorobenzenesulfonyl chloride is disclosed in Gregory, U.S. Pat. No. 2,888,486. The general reaction of aromatic sulfonic acids with thionyl chloride in the presence of catalytic amounts of dimethylformamide to produce the corresponding sulfonyl chloride is disclosed in Bosshard et al., Helvetica Chimica Acta XLII, 1653 (1959), and in Kittila, "Dimethylformamide Chemical Uses", E. I. duPont de Nemours and Co., Chapter 16, pages 76-77. The overall ferric chloride-catalyzed reaction is described, for instance, in Keogh et al., in Robbins, U.S. Pat. No. 3,125,604, and in Huismann, U.S. Pat. No. 2,224,964.

While, as indicated above, the overall chemical reactions that occur in the process are known, the particular combination of process steps of the present invention results in a process having an unexpectedly high efficiency, as will be demonstrated below in the examples.

In a preferred embodiment of the invention, in step (a) of the process monochlorobenzene (MCB) is reacted with sulfur trioxide ($SO_3$) in the presence of at least about 15 mole percent to about 50 mole percent and preferably between about 20 mole percent and 40 mole percent of thionyl chloride ($SOCl_2$) based on $SO_3$. The amount of thionyl chloride present in the reaction medium of step (a) during which monochlorobenzene is reacted with sulfur trioxide is very important to the chemical efficiency of the overall reaction and to the efficiency (isomer efficiency) with which the desired 4,4'-dichlorodiphenyl sulfone isomer is produced. When less than about 15 mole percent of thionyl chloride is used, it has been found that the isomer efficiency is significantly reduced, and when the amount of thionyl chloride is in excess of about 50 mole percent, the chemical efficiency of the process is significantly reduced.

It is preferred to employ excess MCB in step (a) as a reaction medium. Convenient proportions are found within the range of from about 2 to about 3 moles of MCB per mole of $SO_3$. It is usual to employ the $SO_3$ in stabilized form as, for example, in the cyclic trimer form that is known as "Sulfan."

Monosubstituted benzenes (ArX) wherein the substituent is hydrogen, fluoro, bromo or methyl are also suitable for use in the process of the invention. The process is not critical with respect to the mole ratios or in the amount of excess of monosubstituted benzenes to sulfur trioxide that can be used. From a practical standpoint, the ratio of ArX to $SO_3$ does not generally exceed 6:1.

The process of the invention is most advantageously run in an excess of monosubstituted benzene which can then act as the solvent. Other solvents useful in this process include nitrobenzene, $SO_2$, and other liquids known to be relatively inert with respect to $SO_3$.

The reaction of step (a) is rapid, exothermic, and essentially quantitative. While the temperature of the reaction is not critical, (for instance, the operative temperature range may be as broad as from about $-20°$ to $+40°$ C.), it is preferred that the reaction mixture be maintained, for example from about $10°$ C. to about $30°$ C., during the course of the reaction. The temperature can be maintained by the usual means, such as heat exchange means on the reactor, and by controlling the rate of addition of $SO_3$ to the MCB. (The heat of reaction is 70,000 BTU/pound mole or 875 BTU/pound of $SO_3$.)

It is convenient to use atmospheric pressure in step (a), although other pressures may be used. It is desirable to use an inert atmosphere (e.g., nitrogen), for safety reasons, to blanket the reaction mixture throughout the process.

In step (b), at least 60 mole percent of thionyl chloride, based on the $SO_3$, is added to the reaction mixture of step (a) whereby the total amount of thionyl chloride therein will be in at least a slight molar excess. The stoichiometric amount of $SOCl_2$ would be 1 mole of $SOCl_2$ added in steps (a) and (b) per mole of $SO_3$ used in step (a). A minimum of at least about 10 percent excess over the stoichiometric amount should be used, and an excess of about 15 to 50 percent over the stoichiometric has been found to be convenient.

The chemical and overall efficiency of the process of the invention will be even further improved by using very pure $SOCl_2$ containing as small a proportion of sulfur chlorides as practical. A proportion of sulfur chlorides in the $SOCl_2$ of less than about 0.4 weight percent, and preferably about 0.2 weight percent, is most advantageously employed. When the $SOCl_2$ contains more sulfur chlorides than about 0.8 to 1.0 weight percent, the chemical efficiency of the process is significantly reduced, since the sulfur chloride participates in undesired side reactions.

Thionyl bromide can be used interchangeably with thionyl chloride and, as used herein, the term "thionyl chloride" is intended to include thionyl bromide.

Preferably, small catalytically effective amounts of a catalyst such as dimethylformamide (DMF) is employed in step (b). It is preferred to employ the DMF in the smallest amount that is catalytically effective so that it will not be necessary to either remove it prior to step (d), or to use correspondingly more ferric chloride in step (d). The minimum catalytically effective amount of DMF is about two mole percent, based on moles of $SO_3$, but when the quality of the thionyl chloride is that generally commercially obtained, smaller amounts of DMF may be used (the exact amount needed can be determined by routine experimentation).

Step (b) can be carried out by adding the thionyl chloride, preferably with DMF, to the reaction mixture of step (a) at a moderate temperature, e.g. about 25° C. to 30° C., and then heating the reaction mixture at a gradual rate up to about 70° C., and preferably up to about 55° C. to 60° C. The rate of heating has been found to be important, and in general, controlling the rate of heating to affect a temperature increase of up to about 0.5° C./min., and preferably between about 0.25° C./min. and 0.3° C./min., improves the chemical efficiency of the process. The controlled rate of heating permits more conversion of chlorobenzene sulfonic acid to the chlorobenzene sulfonyl chloride to occur at a lower temperature, reduces decomposition of thionyl chloride, and reduces the formation of by-products.

Alternatively, step (b) may be carried out by adding thionyl chloride to the reaction mixture of step (a) continuously, in a step wise manner, while maintaining the temperature of the reaction between about 25° C. and 70° C.

Upon completion of the thionyl chloride addition and gradual heating of the reaction mixture to a temperature of about 70° C., step (c) is carried out by gradually heating the reaction mixture of step (b) to complete the reaction and affect a temperature at which excess unreacted thionyl chloride will be fully removed from the reaction mixture. Preferably, step (c) can be carried out by heating the reaction mixture of step (b) at a substantially constant rate to a temperature of about 155° C. to 160° C. and maintaining the temperature for 15 to 30 minutes or until the termination of gas evolution is detected.

It is desirable to maintain a pressure of from about 1.1 to 1.2 atmospheres on the reaction mixture during step (b) and step (c) to provide a driving force to push the off-gases $SO_2$ and HCl through the scrubber used to absorb these off gases. Otherwise, selection of the pressure is not at all critical.

For steps (a), (b), and (c), a standard glass-lined reactor with corrosion resistant auxiliary means may be used. In commercial scale operations, it is desirable to use a separate reactor for step (d) in order to avoid contamination of the reaction mixtures of steps (a), (b), and (c) with ferric chloride.

The reaction mixture of step (c) is charged to the reaction vessel, along with catalytic quantities of ferric chloride, e.g., a minimum of about 3 to 4 mole percent, based on $SO_3$, more than the moles of DMF that may have been charged during step (b). There is no advantage in using more.

Additional MCB is added to flush out the lines, and with the ferric chloride (which is added as a slurry in MCB). MCB may also be added from time to time during the course of step (d) in order to maintain the desired temperature by refluxing. The total amount of MCB added will usually be enough to provide a concentration of about 65 to 70 weight percent of sulfone product in MCB. Usually, a total of approximately one additional mole of MCB, per mole of $SO_3$ charged to step (a), will be added during the course of step (d).

A relatively narrow temperature range (130°–160° C.) is suggested for step (d) as a compromise between two slow a reaction rate and color body formation, but a starting temperature of between 130° C. to 140° C. is suggested. At about 155° C., the reaction of step (d) takes about 12 hours. The progress of the reaction can be followed by titrating the off-gas (convenient for lab scale), or by analyzing the reaction mixture by gas chromatography for residual sulfonyl chloride content.

A pressure of about 1.1 to 1.2 atmospheres is convenient to employ in step (d). Corrosion resistant equipment should be employed.

At the completion of the reaction, additional MCB is added to dilute the sulfone to a concentration of about 40 weight percent, based on total solution weight (this is done to maintain the sulfone in solution during cooling and washing). The reaction mixture is then cooled to about 70° C., washed with water to remove ferric chloride, and the 4,4'-dichlorodiphenyl sulfone product is recovered by standard means, as by crystallization. A further advantage found with the process of the invention is a reduction in corrosion problems generally associated with the recovery equipment.

Although, as pointed out herein, the general overall chemical reactions that occur in the process of the present invention are known, and in U.S. Pat. No. 3,701,806 to Keogh et al. a process is disclosed that has been used commercially in the preparation of 4,4'-dichlorodiphenyl sulfone, the particular combination of process steps and conditions of the present invention as hereinabove described result in a process having a surprisingly and unexpectedly high efficiency in both the laboratory and during commercial operations. It has also been found that, not only is there high chemical efficiency in preparing an essentially pure mixture of diaryl sulfones and aryl sulfonyl chlorides, but the efficiency of the further reaction of the mixture to obtain substantially complete conversion thereof to diaryl sulfone, and particularly the 4,4'-dichlorodiphenyl sulfone isomer, is also quite good. When used under commercial production conditions, the process of the invention affords more efficient and economical preparation of 4,4'-dichlorodiphenyl sulfone, which product has less color impurity, as compared to commercial operations wherein, for example, the process disclosed in Keogh et al. was employed.

The invention will become more clear when considered together with the following examples which are set forth as being merely illustrative of the invention and which are not intended, in any manner, to be limitative thereof. Unless otherwise indicated, all parts and percentages are by weight.

EXAMPLE 1

Step (a)

Two hundred and forty three grams (2.16 moles) of monochlorobenzene and forty three grams (0.36 moles) of thionyl chloride (0.8 weight percent sulfur chlorides) are charged to a ½-liter glass reactor equipped with thermometer, dropping funnel, stirrer, and reflux condenser. Sulfur trioxide (sulfan), 81.7 grams (1.02 mole), is added at a constant rate over a period of about 50 minutes. During this period, the temperature is maintained by cooling at about 17° C. to 33° C.

Step (b)

N,N-dimethylformamide (2.3 grams; 0.031 moles; and thionyl chloride (125 grams; 1.05 mole; 0.8 weight percent sulfur chlorides) are added to the reaction mixture of step (a) at a temperature of about 30° C., in the same reaction vessel used in step (a). The reflux condenser is attached at the top to an alkaline scrubber. Off-gas evolution begins immediately. The off-gas is absorbed in the scrubber in an aqueous sodium hydroxide solution of known titer. The progress of the reaction is followed by an incremental addition of sodium hydroxide to the solution.

The reaction mixture is heated by a heating mantle, using a "Variac" control. The reaction mixture is heated at a substantially constant rate of 0.23° C./min. to a temperature of 70° C. over a period of about 3 hours.

Step (c)

The reaction mixture of step (b) is then heated at a substantially constant rate of 0.6° C./min. to a temperature of 155° C. over a period of about 2½ hours after which time evolution of off-gas ceases and excess thionyl chloride is distilled.

Step (d)

To the reaction mixture of step (c), 9.7 grams (0.06 mole) of ferric chloride are added at a temperature of 29° C. The mixture is heated to reflux at 135° C. About 40 grams of additional monochlorobenzene is added to the reaction mixture to maintain the reflux. The reaction is followed by off-gas measurement for about one hour as in step (b), then allowed to run over-night. After a period of 12 hours the reactor is cooled to ambient temperature. The reaction mixture is then heated to 155° C. for about one hour until evolution of off-gas ceases. The reaction mixture is diluted with MCB to a 40 percent concentration of sulfone, cooled to 70° C., washed with water to remove ferric chloride, and dichlorodiphenyl sulfone is recovered. A total of 265.3 grams (0.924 moles) of sulfone are produced, 91.3 percent of which is the desired 4,4'-dichlorodiphenyl sulfone isomer, with the chemical efficiency, based on sulfur trioxide, being 90.6 percent.

EXAMPLE 2

This example shows the differences in chemical efficiency and isomer efficiency of a process for preparing 4,4'-dichlorodiphenyl sulfone isomer when the reaction of sulfur trioxide and monochlorobenzene is carried out in the presence of varying amounts and quality of thionyl chloride. The process equipment described in Example 1 is used in carrying out the processes of this Example.

Process A: Step (a)

A charge of 280 grams (2.49 moles) of monochlorobenzene is placed in the reactor and 93.4 grams (1.17 mole) of sulfur trioxide (Sulfan) is added at a constant rate over a period of about 60 minutes. During this period, the temperature is maintained, by cooling, at about 30° C. to 40° C.

Step (b)

A mixture of 185 grams (1.55 moles) of thionyl chloride (0.8 weight percent of sulfur chlorides) and 1.70 grams of N,N-dimethylformamide (0.023 moles) are added to the reaction mixture of step (a) at a temperature of about 30° C. Off-gas evolution begins immediately.

The reaction mixture is heated at a substantially constant rate of about 0.5° C./min. to a temperature of 155° C. over a period of 4 hours, after which time evolution of off-gas ceases and excess thionyl chloride is distilled.

Step (c)

To the reaction mixture of step (b), 9.9 grams (0.06 moles) of ferric chloride are added at a temperature of 135° C. and the mixture is heated to reflux at 155° C. Additional monochlorobenzene is periodically added to maintain the reflux at 155° C. After a period of 12 hours, evolution of off-gas ceases, and the reaction mixture is diluted with MCB to a 40 percent concentration of sulfone, cooled to 70° C., washed with water to remove ferric chloride, and dichlorodiphenyl sulfone is recovered. A total of 310.2 grams (1.08 moles) of sulfone are produced, 89.5 percent of which is the 4,4'-isomer. The chemical efficiency of the process is summarized in Table I, below.

Process B

This process is carried out using the procedure described in U.S. Pat. No. 3,701,806 to Keogh et al.

Step (a)

A mixture of 337.5 grams (3.0 moles) of monochlorobenzene and 193 grams (1.62 moles) of thionyl chloride (0.8 weight percent sulfur chlorides) are charged to the reactor and 82.0 grams (1.02 moles) of sulfur trioxide is added at a constant rate over a period of about 60 minutes. During this period the temperature is maintained by cooling to about 30° C. After the sulfur trioxide addition is complete, heat is applied at a substantially constant rate over a period of about 3 hours to a temperature of about 130° C., and then heating is continued to a temperature of about 155° C. for thirty minutes, at which temperature evolution of off-gas ceases and excess thionyl chloride is distilled.

Step (b)

To the reaction mixture of step (a), 5.3 grams (0.032 moles) of ferric chloride are added at a temperature of about 90° C. and the mixture is heated to reflux at 160° C. to 165° C. Additional monochlorobenzene is added periodically to maintain the reflux. After a period of about 3½ hours, the reaction mixture is heated at 160° C. to 165° C. for about one hour until evolution of off-gas ceases. The reaction mixture is diluted with MCB to a 40 percent concentration of sulfone, cooled to 70° C., washed with water to remove ferric chloride, and dichlorodiphenyl sulfone is recovered. A total of 279 grams (0.97 moles) of sulfone are produced, 91.9% of which is the 4,4'-isomer. The chemical efficiency of the process is summarized in Table I, below.

Process C: Step (a)

A mixture of 241.0 grams (2.14 moles) of monochlorobenzene and 42.1 grams (0.35 moles) of thionyl chloride (0.2 weight percent of sulfur chloride) is charged to the reactor and 80.1 grams (1.0 mole) of sulfur trioxide (Sulfan) is added at a constant rate while the temperature is maintained, by cooling, at 5° C. to 25° C.

Step (b)

A mixture of 120 grams (1.0 moles) of thionyl chloride (0.2 weight percent of sulfur chloride) and 2.3 grams (0.030 moles) of N,N-dimethylformamide is added to the reaction mixture of step (a) at a temperature of about 30° C. The mixture is heated at a substantially constant rate of 0.27° C./min. to a temperature of 69° C.

Step (c)

The reaction mixture of step (c) is then heated at a substantially constant rate to a temperature of 155° C. over a period of about 2 hours after which time evolution of off-gas ceases and excess thionyl chloride is distilled.

Step (d)

The reaction mixture of step (c) is cooled and 8.8 grams (0.054 moles) of ferric chloride are added. The mixture is then heated to reflux at 135° C. and held for 12 hours while additional monochlorobenzene is periodically added to maintain the reflux. The reaction mixture is then diluted with MCB, cooled, and washed with water to remove the ferric chloride. A total of 274.8 grams of dichlorodiphenyl sulfone are produced of which 91.2% is the desired 4,4'-isomer. The chemical efficiency of the process is summarized in Table I, below.

Process D:

Using the procedure described above for Process C, 84.06 grams (0.71 moles) of thionyl chloride (0.8 weight percent sulfur chloride), 242.71 grams (2.16 moles) of monochlorobenzene, and 80.92 grams (1.01 moles) of sulfur trioxide are reacted during step (a); during step (b), 84.68 grams (0.71 moles) of thionyl chloride (0.8 weight percent sulfur chlorides) and 2.38 grams (0.03 moles) of N,N-dimethylformamide are added to the reaction mixture, the reaction mixture then being heated at a constant rate of 0.32° C./min. to a temperature of 70° C. During step (d), 10.11 grams (0.063 moles) of ferric chloride are added to the reaction mixture. The dichlorodiphenyl sulfone product contains 91.3% of the desired 4,4'-isomer. The chemical efficiency of the process is summarized in Table I, below.

TABLE I

| Process | Mole % $SOCl_2/SO_3$ during step (a) | Total Mole % $SOCl_2/SO_3$ | Quality of $SOCl_2$ (approx. weight % of sulfur chlorides) | Chemical Efficiency (%) | Isomer Efficiency (%) | Residue (% Solids) |
|---|---|---|---|---|---|---|
| A | None | 132.5 | .08 | 88.9 | 89.5 | 4.8 |
| B | 159 | 159 | .08 | 86.0 | 91.9 | 4.5 |
| C | 35 | 135 | .02 | 95.0 | 91.2 | 1.28 |
| D | 70 | 140.6 | .08 | 89.3 | 91.3 | 1.22 |

As can be determined from Table I, Process C exhibits a significantly greater chemical efficiency than either Process A, B, or D with a lower residue formation than Process A or B. Process D exhibits a significantly lower chemical efficiency than Process D, but shows an isomer efficiency that is similar to that of Process B and C and residue formation that is lower than Process A and B.

What is claimed is:

1. A process for preparing 4,4'-dichlorodiphenyl sulfone which comprises:
   (a) reacting monochlorobenzene with sulfur trioxide in the presence of at least about 15 mole percent to about 50 mole percent of thionyl chloride, based on the sulfur trioxide, at a temperature from about the freezing point of the reactants to about 40° C.;
   (b) adding to the reaction product mixture of step (a) at least about 60 mole percent thionyl chloride based on the sulfur trioxide wherein the total amount of thionyl chloride added is at least about 110 mole percent based on the sulfur trioxide while maintaining the reaction mixture at a temperature up to about 70° C.;
   (c) continuing the reaction up to a temperature at which excess thionyl chloride will be stripped from the reaction mixture; and
   (d) reacting the products of step (c) with monochlorobenzene in the presence of ferric chloride catalyst to produce 4,4'-dichlorodiphenyl sulfone.

2. The process of claim 1 wherein step (b) of the process is carried out in the presence of a small catalytic amount of N,N-dimethylformamide.

3. The process of claim 2 wherein step (b) of the process is carried out by adding thionyl chloride to the reaction mixture at a temperature about 25° C. to 30° C. and the reaction mixture is heated at a rate of up to about 0.5° C./min.

4. The process of claim 2 wherein in step (a) between about 20 mole percent and 40 mole percent of thionyl chloride, based on the sulfur trioxide, is used.

5. The process of claim 1 wherein the thionyl chloride contains up to about 1.0 weight percent of sulfur chlorides.

* * * * *